(12) United States Patent
Moe

(10) Patent No.: US 6,478,819 B2
(45) Date of Patent: Nov. 12, 2002

(54) PROSTHETIC HEART VALVES WITH FLEXIBLE POST GEOMETRY

(75) Inventor: Riyad E. Moe, Austin, TX (US)

(73) Assignee: Sulzer Carbomedics Inc., Austin, TX (US)

(*) Notice: Subject to any disclaimer, the term of this patent is extended or adjusted under 35 U.S.C. 154(b) by 0 days.

(21) Appl. No.: 09/321,325

(22) Filed: May 27, 1999

(65) Prior Publication Data

US 2001/0049556 A1 Dec. 6, 2001

(51) Int. Cl.[7] .................................. A61F 2/24; A61F 2/06
(52) U.S. Cl. ...................... 623/2.18; 623/2.12; 623/1.26
(58) Field of Search .................................. 623/2.1, 2.17, 623/2.18, 2.14, 2.38, 1.24, 1.25, 1.26, 2.11, 23.64

(56) References Cited

U.S. PATENT DOCUMENTS

| | | | | |
|---|---|---|---|---|
| 4,106,129 A | * | 8/1978 | Carpentier et al. | 3/1.5 |
| 4,501,030 A | * | 2/1985 | Lane | 3/1.5 |
| 4,605,407 A | * | 8/1986 | Black et al. | 623/2 |
| 5,037,434 A | * | 8/1991 | Lane | 623/2 |
| 5,855,601 A | * | 1/1999 | Bessler et al. | 623/2 |
| 5,895,420 A | * | 4/1999 | Mirsch, II et al. | 623/2 |

FOREIGN PATENT DOCUMENTS

| | | | | |
|---|---|---|---|---|
| EP | 0856300 | * | 8/1998 | 623/2.11 |

* cited by examiner

Primary Examiner—Corrine McDermott
Assistant Examiner—Alvin Stewart
(74) Attorney, Agent, or Firm—Timothy L. Scott; Philip S. Lyren

(57) ABSTRACT

A stent includes an elongated stent member having a plurality of post members. Each post member includes a pair of opposite sides. A first end of each post member includes an arcuate apex interconnecting the opposite sides. A second end of each post member has an open end. The opposite sides are angled to converge toward each other at the second end. The second end of each post member is connected to an adjacent post member by a stent portion. Each opposite side and each stent portion converge at an angle of less than 90°. The opposite sides are angled to converge toward each other at the second end.

13 Claims, 3 Drawing Sheets

PROSTHETIC HEART VALVES WITH FLEXIBLE POST GEOMETRY

BACKGROUND

The disclosures herein relate generally to flexible leaflet prosthetic heart valves and more particularly to a wire stented valve including posts having a lengthened trajectory.

Heart valves, of the tissue type and the flexible polymer type, require a stent that deflects under load, yet remains below a design stress. In fact, the lower the stress, the better the fatigue resistance. An objective, therefore, is a structure with a high ratio of stent flexibility to stent stress. Another objective is to stay within the tight anatomical envelope of the aorta.

Various stented valve devices have been proposed. U.S. Pat. No. 4,106,129 discloses a supported bioprosthetic heart valve in which the supporting stent is capable of annular deformation and also of limited perimetric expansion and contraction during heart operation. The stent includes a wire frame composed of a single flexible wire preformed to define inverted U-shaped commissure supports merging smoothly with arcuate portions connecting such supports.

In U.S. Pat. No. 4,343,048, a stent for a cardiac valve comprises a base ring having metal legs projecting therefrom in a generally axial direction, each leg being flexible in such a manner that, when the stent has a valve installed therein and the valve is under pressure such as when operating in the heart, each respective leg can resiliently deform over substantially its whole axial length to take up strain in the valve without impairing its performance.

U.S. Pat. No. 4,501,030 discloses a prosthetic heart valve including a frame having a plurality of commissure supports, a plurality of resilient supports, and a plurality of valve leaflets. The valve leaflets are attached to the resilient supports, and the resilient supports lie radially outwardly of the commissure supports, respectively. When in use, the valve is subjected to forces which are used to clamp the valve leaflets between the resilient supports and the commissure supports to augment whatever other leaflet attachment techniques may be used.

U.S. Pat. No. 5,037,434 discloses a bioprosthetic heart valve comprising first and second mechanisms for supporting leaflets to provide multiple effective spring constants. An inner frame supporting commissures of the valve is elastic, permitting the commissures to bend in toward the center of the prosthetic heart valve at very low loads. A relatively rigid annular support ring supports the elastic frame and provides the second spring constant mechanism. An attachment system for sewing bioprosthetic leaflets to the frame and clamping the leaflets between the frame and the annular ring minimizes stress risers in the leaflets. The leaflets have an uncoupled mating edge where the leaflets meet in the center of the valve. The uncoupled portions of the leaflets permit the leaflets to roll by each other.

U.S. Pat. No. 5,545,215 discloses a frame to be placed as an external support of a biological valved conduit containing three leaflets. This external frame, made of biocompatible metal or plastic is sutured to the outer surface of the valved conduit made of biological or biocompatible membrane or sigmoid valve root in order to maintain its natural geometry. The frame has a general cylindrical configuration, circular as viewed from above and below. From a side view however, both upper and lower ends of the cylinder present three convex curvatures joined at equidistant points of the circumference. These upper and lower curves are joined by three vertical struts, so that three large saddle shaped paraboloid gaps result. The frame is a wire-like structure.

U.S. Pat. No. 5,562,729 discloses a multi-leaflet heart valve composed of biocompatible polymer which simultaneously imitates the structure and dynamics of biological heart valves. The valve includes a plurality of flexible leaflets dip cast on a mandrel. The leaflets are then bonded with a bonding agent to the interior surfaces of a plurality of struts on a metal-reinforced prosthetic stent. The leaflets open and close in response to the pumping action of the heart.

To improve the flexibility of a wire stent, a thinner or finer wire can be used. Flexibility will be increased, but so will the maximum stress encountered in the stent. Conversely, to reduce the stresses in a wire stent, a thicker wire can be used but flexibility is sacrificed. A wire stent with a crimp collar is analogous to a thickened section, and flexibility of the stent is lost adjacent the crimp collar.

A flat pattern stent can reduce stress by use of larger sections at regions of high stress. However, flexibility is also reduced. In fact, the highest flexibility is achieved with a uniform cross-section. Thinning a section locally effectively increases the remaining sections.

Flexibility can be increased by increasing the stent height, but this has the potential of interfering with aortic anatomy. Similarly, increasing the diameter of the valve will increase flexibility, but is not suitable for small aortas. Changing materials is also an option but medically acceptable alloys are limited.

Therefore, what is needed is a stent with a uniform cross-section and a high ratio of stent flexibility to stent stress.

SUMMARY

One embodiment, accordingly, provides a stent with uniform cross-section, lengthened trajectory and a high ratio of stent flexibility to stent stress. To this end, a stent includes an elongated stent member having a plurality of flexible post members. Each post member includes a pair of opposite sides. A first end of each post member has an apex which interconnects the opposite sides. A second end of each post member is an open end. The opposite sides are angled to converge toward each other at the second end.

A principal advantage of this embodiment is that, a stent may be provided with a high ratio of stent flexibility to stent stress while remaining within the prescribed valve envelope.

BRIEF DESCRIPTION OF THE DRAWING FIGURES

DETAILED DESCRIPTION

Figure 1:
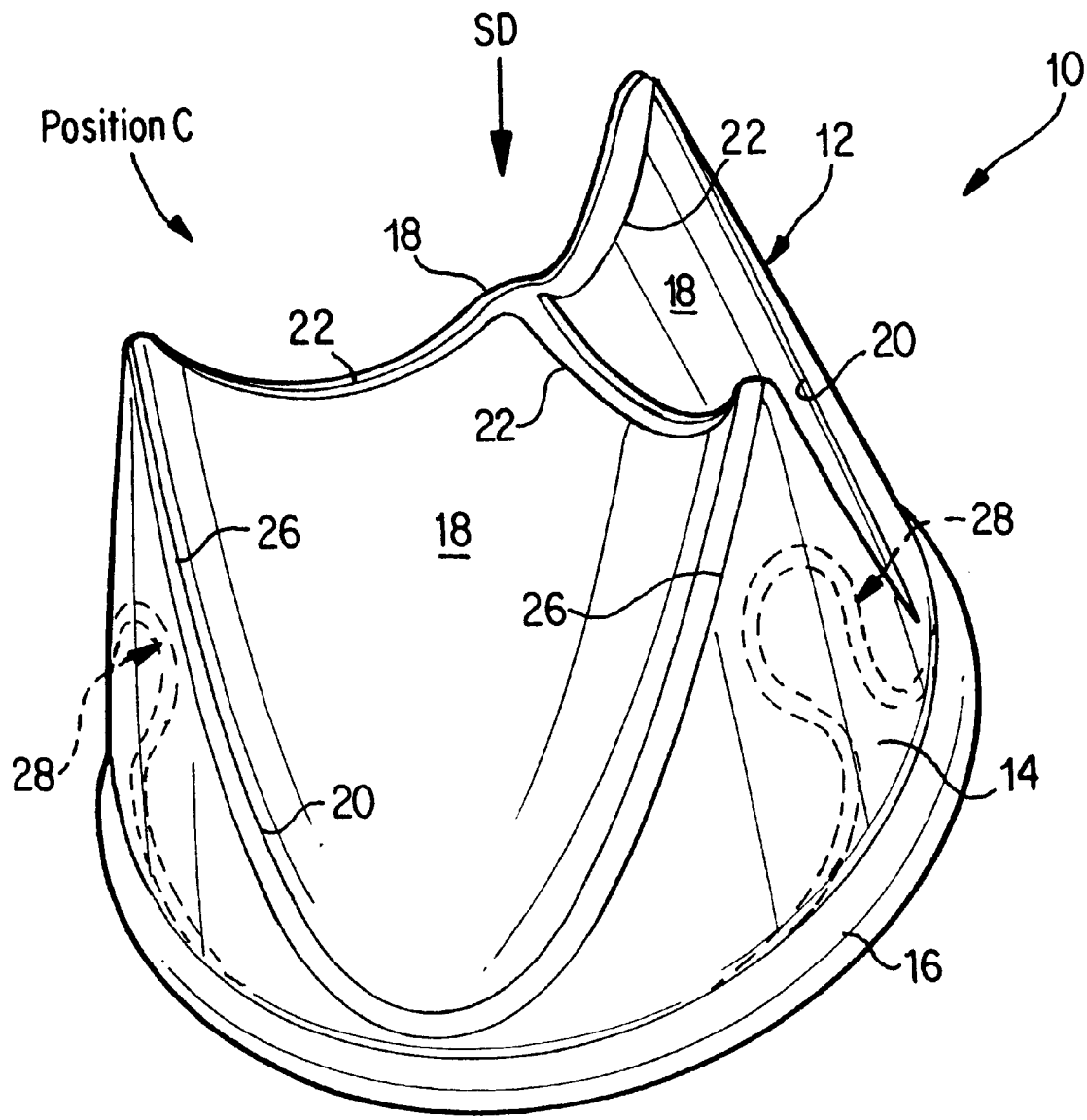
FIG. 1 is an isometric view illustrating an embodiment of a prosthetic heart valve in an at rest position.
Figure 2:
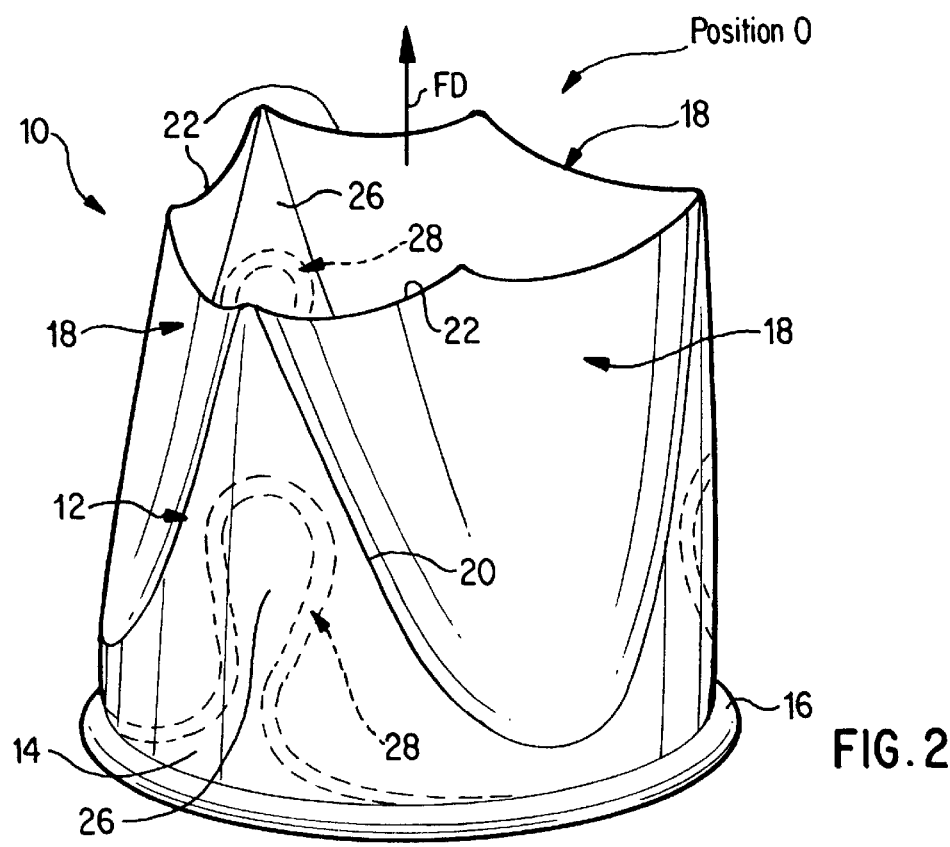
FIG. 2 is an isometric view illustrating an embodiment of a prosthetic heart valve in an open position.

A heart valve is generally designated 10 in FIG. 1. Heart valve 10 is formed as a one-piece molded biocompatible polymer body such as silicone or polyurethane and includes a generally annular peripheral body portion 12 which has a base 14. A sewing ring 16 may be formed with the base 14. Three flexible leaflets 18 are formed with body 12 and extend from an attachment curve 20 to terminate at a free margin 22. In FIG. 1, the valve is in a natural-state condition, i.e. the valve parts are at rest and are not under the influence of any pressure acting thereon. This is in contrast with the valve after installation when the pumping action of the heart sequentially and repeatedly opens and closes the valve by urging the leaflets 18 in a first or opening direction indicated by the arrow designated FD, FIG. 2, and then in a second or closing direction, opposite the first direction, indicated by the arrow designated SD, FIG. 1.

The attachment curve 20 defines a coupling between each leaflet 18 and the peripheral body 12, and also defines a plurality of shaped posts 26 which comprise a portion of body 12 which is of a greater thickness relative to leaflets 18. A flexible stent 28, made of wire or plastic, is embedded in valve 10 by being molded into posts 26. In some configurations of molded or tissue valves, stent 28 may be secured to an outside surface of the valve by sutures, however, the purpose of the stent in either configuration is to provide flexible reinforcement to the opening and closing valve body as described above.

Figure 3:
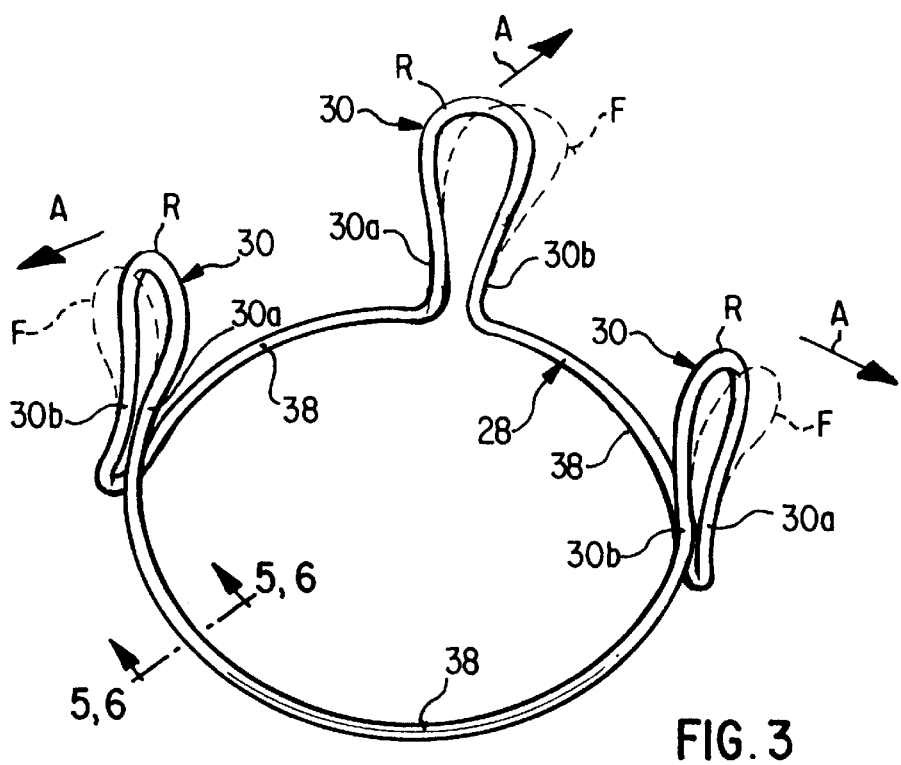
FIG. 3 is an isometric view illustrating an embodiment of a stent member having multiple posts.

Stent 28, FIG. 3, comprises an elongated stent member having a plurality of flexible post members 30. The post members 30 are formed into the stent 28 and each post member includes a pair of opposite sides 30*a* and 30*b*. When valve 10 is in an at rest position C, FIG. 1, stent posts 30 are in a natural or at rest position R, as illustrated in solid lines in FIG. 3. When valve 10 is in an open position O, FIG. 2, stent posts 30 are flexed outwardly in the direction illustrated by a plurality of directional arrows designated A, to a flexed or broken line position F.

Figure 4:
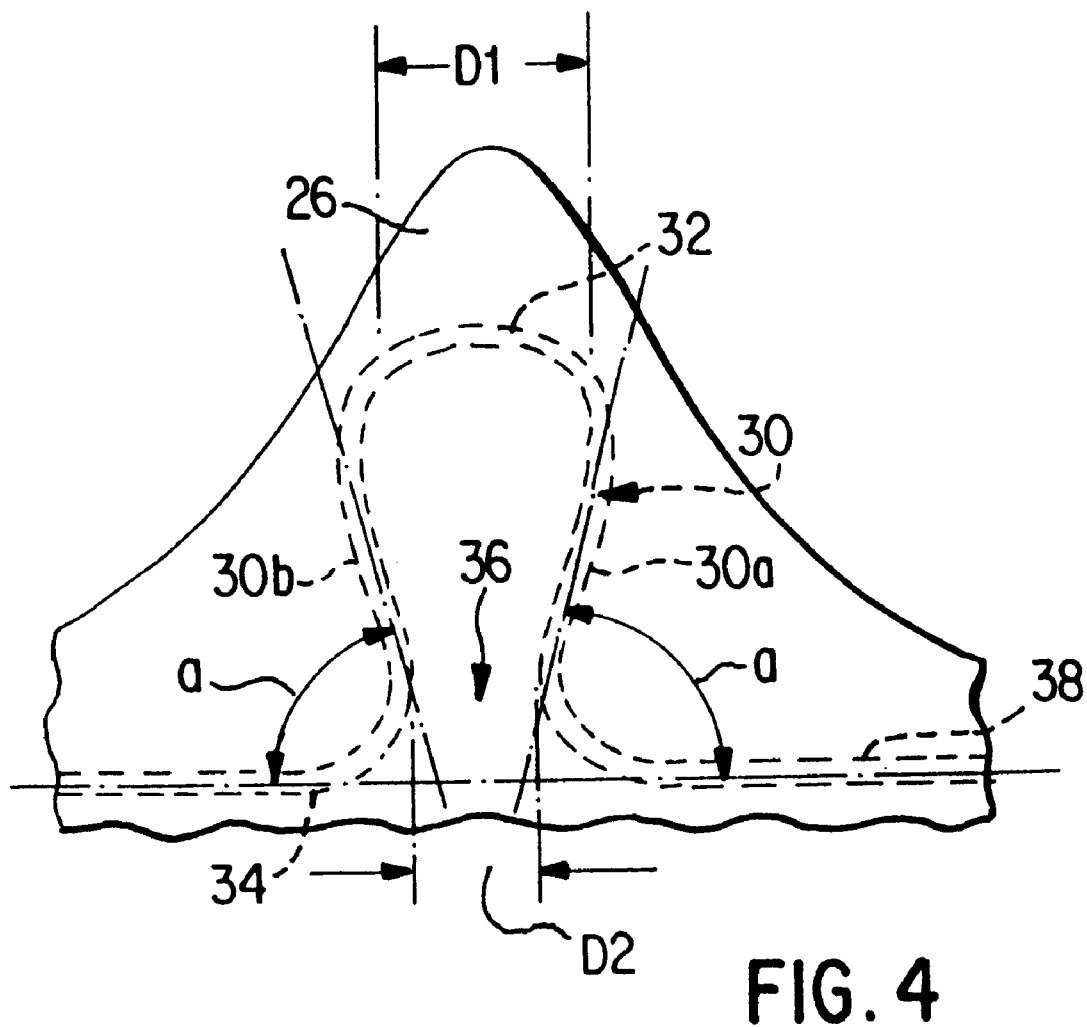
FIG. 4 is a partial view illustrating an embodiment of a post member embedded in a post.

Each post member 30, FIG. 4, is embedded in a post 26 and includes a first end 32 and a second end 34 opposite first end 32. First end 32 forms an apex of post member and is of an arcuate shape. Second end 34 includes an opening 36, that is, opposite sides 30*a* and 30*b* converge toward each other at second end 34 but do not engage, thus forming the opening 36.

The spaced apart sides 30*a* and 30*b*, of each post member 30 are spaced apart by a first distance D1 adjacent the first end 32, and are spaced apart by a second distance D2 adjacent the second end 34, such that the first distance D1 is greater than the second distance D2.

Each post member 30 is connected to each other post member 30 by a stent portion 38, FIGS. 3 and 4. Side 30*a* of each post 30 converges with a respectively adjacent stent portion 38 at an angle a less than 90°. Likewise, side 30*b* of each post 30 converges with a respectively adjacent stent portion 38 at an angle less than 90°. This results from the sides 30*a* and 30*b* converging toward each other as stated above.

Figure 5:
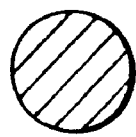
FIG. 5 is a cross-sectional view illustrating an embodiment of a stent.
Figure 6:
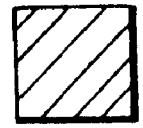
FIG. 6 is a cross-sectional view illustrating another embodiment of a stent.

Stent 28 has a uniform cross-section at X—X, FIG. 3, along the entire length thereof. For example, the cross-section may be circular, FIG. 5, or rectangular, FIG. 6, but in either case it is a solid and uniform cross-section for greatest flexibility.

As a result, one embodiment provides a stent having a plurality of flexible post members. Each post member includes a pair of opposite sides. A first end of each post member includes an apex which interconnects the opposite sides. A second end of each post member is an open end. The opposite sides are angled to converge toward each other at the second end.

Another embodiment provides a prosthetic heart valve including a stent attached to the valve and having a plurality of flexible post members. Each post member includes a pair of opposite sides. A first end of each post member includes an apex which interconnects the opposite sides. A second end of each post member is an open end. The opposite sides are spaced apart by a first distance adjacent the apex, whereas the opposite sides are spaced apart by a second distance adjacent the second end, the second distance being less than the first distance.

A further embodiment provides a stent for a flexible leaf prosthetic heart valve including a stent having a plurality of flexible post members. Each post member includes a pair of opposite sides. A first end of each post member has an apex which interconnects the opposite sides. A second end of each post member is an open end. The second end of each post member is connected to an adjacent post member by a stent portion. Each opposite side and each stent portion converge at an angle of less than 90°.

As it can be seen, the principal advantages of these embodiments are that, in contrast with previously described devices, a stent having a uniform cross-section and lengthened trajectory, has a high ratio of stent flexibility to stent stress. The trajectory can be lengthened, while remaining within the prescribed valve envelope, by decreasing the base radius and/or increasing the stent leg angle beyond vertical, for example. This provides increased flexibility at nearly identical peak stress. If lower stress is needed, flexibility can be increased by trajectory length and stress can be reduced by section thickness. These parameters can be manipulated until the desired flexibility/stress combination is achieved. Also, this can be implemented in formed wire or a flat pattern. Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A prosthetic heart valve comprising:
   1) an annular valve body comprising a flexible material, said valve body having
      A) a circumference and a plurality of valve body posts spaced around said circumference, each of said valve body posts having first and second ends, each of said first ends comprising a body post apex,
      B) an attachment curve coupling each pair of adjacent body post apices, and
      C) a plurality of flexible leaflets, each leaflet being coupled to an attachment curve; and
   2) a stent coupled to the valve body, said stent comprising a plurality of flexible stent post members, each of said stent post members being coupled to a valve body post and having first and second ends, a pair of opposite sides, and a uniform cross-section,
      A) each of said first ends comprising an arcuate stent post apex interconnecting the opposite sides,
      B) each of said second ends being open,
      C) each said pair of opposite sides being spaced apart by a first distance adjacent the apex and a second distance, less than the first distance, adjacent the second end.

2. The prosthetic heart valve of claim 1 wherein said stent further comprises at least one stent portion interconnecting two adjacent stent post members.

3. The prosthetic heart valve of claim 2 wherein said stent further comprises a plurality of stent portions and the second end of each stent post member is coupled to the second end of an adjacent stent post member by a stent portion.

4. The prosthetic heart valve of claim 3 wherein each side of a stent post member and each stent portion connected to said side of a stent post member converge at an angle of less than 90°.

5. The prosthetic heart valve of claim 1 wherein the stent has a circular cross section.

6. The prosthetic heart valve of claim 1 wherein the stent is embedded in the valve body.

7. The prosthetic heart valve of claim 1 wherein the stent is coupled to an outside surface of the valve body.

8. The prosthetic heart valve of claim 1 wherein the stent has a rectangular cross section.

9. The prosthetic heart valve of claim 1 wherein the flexible material is a polymer.

10. The prosthetic heart valve of claim 9 wherein the polymer comprises silicone.

11. The prosthetic heart valve of claim 9 wherein the polymer is polyurethane.

12. The prosthetic heart valve of claim 1 wherein the flexible material comprises tissue.

13. The prosthetic heart valve as defined in claim 1 further comprising a sewing ring coupled to said valve body.

* * * * *